United States Patent [19]

Lesher et al.

[11] Patent Number: 4,486,431

[45] Date of Patent: * Dec. 4, 1984

[54] CARDIOTONIC USE OF 4,5-DIHYDRO-6-(4-PYRIDINYL)-3(2H)-PYRIDAZINONES

[75] Inventors: George Y. Lesher, Schodack; William B. Dickinson, Albany, both of N.Y.

[73] Assignee: Sterling Drug Inc., New York, N.Y.

[ * ] Notice: The portion of the term of this patent subsequent to Jun. 29, 1999 has been disclaimed.

[21] Appl. No.: 245,086

[22] Filed: Mar. 18, 1981

Related U.S. Application Data

[63] Continuation-in-part of Ser. No. 225,024, Jan. 14, 1981, abandoned, which is a continuation-in-part of Ser. No. 71,064, Aug. 30, 1979, Pat. No. 4,298,609.

[51] Int. Cl.³ .............................................. A61K 31/50
[52] U.S. Cl. .................................. 424/250; 544/238; 544/239
[58] Field of Search ................. 544/238, 239; 424/250

[56] References Cited

U.S. PATENT DOCUMENTS

| | | | |
|---|---|---|---|
| 4,298,609 | 11/1981 | Lesher et al. | 424/250 |
| 4,304,776 | 12/1981 | Lesher et al. | 544/238 |
| 4,304,777 | 12/1981 | Lesher et al. | 424/250 |
| 4,337,253 | 6/1982 | Lesher et al. | 544/238 |
| 4,346,221 | 8/1982 | Lesher et al. | 544/238 |
| 4,404,203 | 9/1983 | Sircar | 544/239 |

FOREIGN PATENT DOCUMENTS 19987 2/1979 Japan .

OTHER PUBLICATIONS

McEvoy and Allen, [J. Org. Chem. 38, 4044–4048 (1978); J. Med. Chem. 17, 281–286 (1974)].
Curran and Ross, [J. Med. Chem. 17, 273–281 (1974)].
Albright, McEvoy and Moran, [J. Heterocyclic Chem. 15, 881–892 (1978)].
McEvoy and Albright, [J. Org. Chem. 44, 4597–4603 (1979)].
Leete et al., [J. Org. Chem. 37, 4465–4466 (1972)].

*Primary Examiner*—Albert T. Meyers
*Assistant Examiner*—Freda L. Abramson
*Attorney, Agent, or Firm*—Robert K. Bair; B. Woodrow Wyatt; Paul E. Dupont

[57] ABSTRACT

4,5-Dihydro-4-R-6-(4-pyridinyl)-3(2H)-pyridazinone (IA) or pharmaceutically-acceptable acid-addition salt thereof, where R is hydrogen or methyl, is shown as the active component in cardiotonic composition and method for increasing cardiac contractility in a patient requiring such treatment. Also shown is the preparation of IA by reacting a lower-alkyl 2-R-4-(BN)-4-cyano-4-(4-pyridinyl)butanoate with hydrazine, where R is hydrogen or methyl, and BN is 4-morpholinyl, 1-piperidinyl or 1-pyrrolidinyl.

3 Claims, No Drawings

CARDIOTONIC USE OF 4,5-DIHYDRO-6-(4-PYRIDINYL)-3(2H)-PYRIDAZINONES

CROSS-REFERENCE TO RELATED APPLICATION

This application is a continuation-in-part of copending application Ser. No. 225,024, filed Jan. 14, 1981 and now abandoned, in turn, a continuation-in-part of copending application Ser. No. 71,064, filed Aug. 30, 1979 and now U.S. Pat. No. 4,298,609, issued Nov. 3, 1981, which discloses and claims 4,5-dihydro-6-(4-pyridinyl)-3-pyridazinol, its preparation and its use for lowering blood pressure.

4,5-Dihydro-6-(4-pyridinyl)-3-pyridazinol, which we now prefer to designate as its tautomeric 4,5-dihydro-6-(4-pyridinyl)-3(2H)-pyridazinone, also is disclosed as an intermediate in the preparation of 6-(4-pyridinyl)-3-pyridazinol or its tautomeric 6-(4-pyridinyl)-3(2H)-pyridazinone in copending application Ser. No. 144,576, filed Apr. 28, 1980 and now U.S. Pat. No. 4,304,777, issued Dec. 8, 1981.

BACKGROUND OF THE INVENTION (a) Field of the Invention

This invention relates to the use of 4,5-dihydro-6-substituted-3(2H)-pyridazinones as cardiotonic agents, to a process for their preparation and to one of them per se.

(b) Description of the Prior Art

The Yoshitomi Pharmaceutical Ind., Ltd. Japanese patent application Disclosure No. 19,987/79, published Feb. 15, 1979 and based on application No. 85,192/77, filed July 15, 1977, discloses, inter alia, the preparation of 4,5-dihydro-6-(4-pyridinyl)-3(2H)-pyridazinone by refluxing for two hours an ethanolic solution of 3-(isonicotinoyl)propanoic acid [same as γ-oxo-γ-(4-pyridinyl)butyric acid] and hydrazine hydrate. 4,5-Dihydro-6-(4-pyridinyl)-3(2H)-pyridazinone and closely related 4,5-dihydro-6-(4- or 3- or 2-pyridinyl)-5-R-3(2H)-pyridazinones, where R is H or lower alkyl, are said (page 2 of English translation) to be "useful not only as medicines such as hypotensive and antithrombus agents because they have pharmacological actions such as hypotensive, blood platelet coagulation-inhibitory and membrane-stablilizing actions, but also as intermediates for the synthesis of such medicines".

McEvoy and Allen [J. Org. Chem. 38, 4044–48 (1978); J. Med. Chem. 17, 281–286 (1974)] show a method for preparing 3-(substituted-benzoyl)-3-substituted-alkanoic acids and their reaction with hydrazine to prepare 6-(substituted-phenyl)-5-substituted-4,5-dihydro-3(2H)-pyridazinones, hypotensive agents.

Curran and Ross [J. Med. Chem. 17, 273–281 (1974)] show the preparation of 6-phenyl-4,5-dihydro-3(2H)-pyridazinones, hypotensive agents, by refluxing the requisite 3-benzoylpropionic acid with hydrazine hydrate in ethanol.

Albright, McEvoy and Moran [J. Heterocyclic Chem. 15, 881–892 (1978)] show the use of α-(substituted-phenyl)-4-morpholineacetonitriles in 1,4-additions to ethyl acrylate, ethyl crotonate, methyl α-methylacrylate, acrylonitrile, methylacrylonitrile, crotononitrile and cinnamonitrile to produce 4-cyano-4-(4-morpholinyl)-4-(substituted-phenyl)butanenitriles and -butanoic acid esters, and their conversion by reaction with hydrazine to 6-(substituted-phenyl)-4,5-dihydro-3(2H)-pyridazinones and, in turn, their dehydrogenation by reaction with bromine to produce 6-(substituted-phenyl)-3-(2H)-pyridazinones optionally bearing methyl at the 4- or 5- position of the pyridazinone ring.

McEvoy and Albright [J. Org. Chem. 44, 4597–4603 (1979)] show, inter alia, the reaction of 2-cyano-2-(4- or 3-pyridinyl)-2-(4-morpholinyl)ethanenitrile with acrylonitrile or ethyl acrylate to produce respectively ethyl 4-cyano-4-(4- or 3-pyridinyl)-4-(4-morpholinyl)butanoate or 4-cyano-4-(4- or 3-pyridinyl)-4-(4-morpholinyl)-butanenitrile.

Leete et al. [J. Org. Chem. 37, 4465–6 (1972)] shows the reaction of 2-(3-pyridinyl)-2-(4-morpholinyl)ethanenitrile with acrylonitrile to produce 4-cyano-4-(3-pyridinyl)-4-(4-morpholinyl)butanenitrile and its conversion by heating it with acetic acid, water and tetrahydrofuran to 4-oxo-4-(3-pyridinyl)butanenitrile.

SUMMARY OF THE INVENTION

In its composition aspect, the invention resides in a cardiotonic composition for increasing cardiac contractility in a patient, said composition comprising a pharmaceutically-acceptable carrier, and as the active component thereof, a cardiotonically-effective amount of 4,5-dihydro-4-R-6-(4-pyridinyl)-3(2H)-pyridazinone or salt thereof, where R is hydrogen or methyl.

In a method aspect, the invention resides in a method for increasing cardiac contractility in a patient requiring such treatment which comprises administering to said patient a medicament comprising a pharmaceutically-acceptable carrier and, as the active component thereof, a cardiotonically-effective amount of 4,5-dihydro-4-R-6-(4-pyridinyl)-3(2H)-pyridazinone or salt thereof.

In a process aspect the invention resides in the process of preparing a 4,5-dihydro-4-R-6-(4-pyridinyl)-3(2H)-pyridazinone which comprises reacting a loweralkyl 2-R-4-(BN)-4-cyano-4-(4-pyridinyl)butanoate with hydrazine, where R is hydrogen or methyl and BN is defined below.

In a composition of matter aspect the invention resides in 4,5-dihydro-4-methyl-6-(4-pyridinyl)-3(2H)-pyridazinone or salt thereof.

DETAILED DESCRIPTION INCLUSIVE OF PREFERRED EMBODIMENTS

The composition aspect of the invention resides in a cardiotonic composition for increasing cardiac contractility, which comprises a pharmaceutically-acceptable carrier and, as the active component thereof, a cardiotonically-effective amount of 4,5-dihydro-4-R-6-(4-pyridinyl)-3(2H)-pyridazinone or pharmaceutically-acceptable acid-addition salt thereof, where R is hydrogen or methyl. The usefulness of 4,5-dihydro-4-R-6-(4-pyridinyl)-3(2H)pyridazinone as a cardiotonic agent was determined by standard pharmacological evaluation procedures.

The method aspect of the invention resides in the method for increasing contractility in a patient requiring such treatment which comprises administering orally or parenterally in a solid or liquid dosage form to such patient a medicament comprising a pharmaceutically-acceptable carrier and, as the active component thereof, a cardiotonically-effective amount of 4,5-dihydro-4-R-6-(4-pyridinyl)-3(2H)-pyridazinone or pharmaceutically-acceptable acid-addition salt thereof, where R is hydrogen or methyl.

The process aspect resides in the preparation of 4,5-dihydro-4-R-6-(4-pyridinyl)-3(2H)-pyridazinone which comprises reacting a lower-alkyl 2-R-4-(BN)-4-cyano-4-(4-pyridinyl)butanoate with hydrazine, where R is hydrogen or methyl and BN is 4-morpholinyl, 1-piperidinyl or 1-pyrrolidinyl.

In a composition of matter aspect the invention resides in 4,5-dihydro-4-methyl-6-(4-pyridinyl)-3(2H)-pyridazinone or pharmaceutically-acceptable acid-addition salt thereof. This compound is useful as a cardiotonic agent, as determined by standard cardiotonic evaluation procedures.

4,5-Dihydro-4-R-6-(4-pyridinyl)-3(2H)-pyridazinone may exist in tautomeric forms, that is, as 4,5-dihydro-4-R-6-(4-pyridinyl)-3(2H)-pyridazinone having the formula IA and/or as 4,5-dihydro-4-R-6-(4-pyridinyl)-3-pyridazinol having formula I, illustrated as follows (Py is 4-pyridinyl):

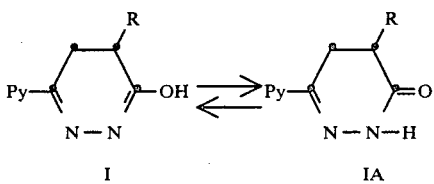

Actually, the two tautomers (I and IA) are so closely interrelated as to be considered essentially one and the same compound and in any given set of circumstances such compound capable of tautomerism can exist in either or both tautomeric forms. Although we have preferred to use the name based on structure IA, it is understood that either or both structures are comprehended herein.

The term "lower-alkyl" as used herein in "lower-alkyl 2-R-4-(BN)-4-cyano-4-(4-pyridinyl)butanoate", means alkyl radicals having from one to six carbon atoms which can be arranged as straight or branched chains, illustrated by methyl, ethyl, n-propyl, isopropyl, 2-butyl, n-butyl, n-hexyl, and the like.

4,5-Dihydro-4-R-6-(4-pyridinyl)-3(2H)-pyridazinone is useful both in the free base form and in the form of acid-addition salts, and both forms are within the purview of the invention. The acid-addition salts are simply a more convenient form for use; and in practice, use of the salt form inherently amounts to use of the base form. The acids which can be used to prepare the acid-addition salts include preferably those which produce, when combined with the free base, pharmaceutically-acceptable salts, that is, salts whose anions are relatively innocuous to the animal organism in pharmaceutical doses of the salts, so that the beneficial cardiotonic properties inherent in the free base are not vitiated by side effects ascribable to the anions. In practicing the invention, it was convenient to utilize the compound of the invention in its free base form. However, appropriate pharmaceutically-acceptable salts with the scope of the invention are those derived from mineral acids such as sulfuric acid, phosphoric acid, hydrochloric acid and sulfamic acid; the organic acids such as methanesulfonic acid, lactic acid, acetic acid, citric acid, tartaric acid, ethanesulfonic acid, benzenesulfonic acid, p-toluenesulfonic acid, cyclohexylsulfamic acid, quinic acid, and the like, giving the sulfate, phosphate, hydrochloride, sulfamate, methanesulfonate, lactate, acetate, citrate, tartrate, ethanesulfonate, benzenesulfonate, p-toluenesulfonate, cyclohexylsulfamate and quinate, respectively.

The acid-addition salts of said basic compound are prepared either by dissolving the free base in an aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

The molecular structure of 4,5-dihydro-6-4-R-(4-pyridinyl)-3(2H)-pyridazinone was assigned on the basis of evidence provided by infrared, nuclear magnetic resonance and mass spectra, and by the correspondence of calculated and found values for elemental analyses.

The manner of making and using the instant invention will now be generally described so as to enable a person skilled in the art of pharmaceutical chemistry to make and use the same, as follows.

The reaction lower-alkyl 2-R-4-cyano-4-(BN)-4-(4-pyridinyl)butanoate with hydrazine to produce 4,5-dihydro-4-R-6-(4-pyridinyl)-3(2H)-pyridinone is carried out by heating the reactants at about 65°–120° C. in a suitable solvent, preferably at about 80°–100° C. in a lower-alkanol. The reaction is preferably run by refluxing the reactants in ethanol. Other lower-alkanols suitable as solvents are methanol, n-butanol, 2-butanol and 2-methyl-n-propanol.

The generally known reaction of 2-(4-pyridinyl)ethanenitrile with lower-alkyl 2-R-2-propenoate to produce lower-alkyl 2-R-4-(BN)-4-cyano-4-(4-pyridinyl)butanoate is carried out under anhydrous conditions by mixing the reactants at about 25° C. to 60° C., preferably about 30° C. to 50° C., in a suitable solvent in the presence of a basic condensing agent. The reaction is conveniently run by mixing the reactants at about 30° C. to 50° C. in dry tetrahydrofuran in the presence of an alkali hydroxide in methanol. Other suitable solvents are other lower-alkanol, e.g., ethanol or isopropyl alcohol, dimethylformamide, acetonitrile, tetrahydrofuran, benzene and the like. Other suitable basic condensing agents include sodium hydroxide, alkali lower-alkoxides, e.g., sodium methoxide or potassium ethoxide, sodium hydride, and the like.

The intermediate 2-R-4-oxo-4-(4-pyridinyl)butanenitriles are generally known compounds, e.g., Stetter et al. Chem. Ber. 107, 210 (1974), Leete et al, J. Org. Chem. 37, 4466 (1972) and Stetter et al. U.S. Pat. No. 4,014,889 (Mar. 29, 1977), and are prepared by generally known methods.

4,5-Dihydro-4-R-6-(4-pyridinyl)-3(2H)-pyridine also can be prepared by reacting 4-oxo-2-R-4-(4-pyridinyl)-butyronitrile with a hydrazine salt of a strong inorganic or organic sulfonic acid to produce 4,5-dihydro-6-(4-pyridinyl)-3(2H)-pyridazinone. This reaction is carried out by heating the reactants at about 65°–120° C. in a suitable solvent, preferably at about 80°–100° C. in a mixture of water and a lower alkanol. The reaction is preferably run by refluxing 4-oxo-2-R-4-(4-pyridinyl)-butyronitrile with hydrazine sulfate in aqueous ethanol. Other hydrazine salts usable are hydrazine dihydrochloride, hydrazine dimethanesulfonate, and the like salts derived from phosphoric acid, ethanesulfonic acid, benzenesulfonic acid, and the like acids. Other lower-alkanols useful as solvents are methanol, n-propanol, 2-propanol, n-butanol, 2-butanol and 2-methyl-n-propanol. Other solvents can be used, e.g., dimethylformamide. This procedure was used for preparing the compound where R is hydrogen in said copending application Ser. No. 71,064.

The intermediate 2-(BN)-2-(4-pyridinyl)ethanenitriles are generally known compounds, e.g., Janssen et al., J. Am. Pharm. Assoc., Sci. Ed., 44 465–7 (1955), and are prepared by generally known methods.

The following examples will further illustrate the invention without, however, limiting it thereto.

1.
4,5-Dihydro-4-methyl-6-(4-pyridinyl)-3(2H)pyridazinone

A mixture containing 15 g. of methyl 4-cyano-2-methyl-4-(4-morpholinyl)-4-(4-pyridinyl)butanoate, 26 ml. of 85% hydrazine hydrate and 220 ml. of absolute ethanol was refluxed with stirring for about seventeen hours and the solvent was distilled off in vauco. The remaining crystalline residue was recrystallized from ethyl acetate, dried at 90° C. and combined with another sample of the same compound prepared by the same procedure starting with 11 g. of methyl 4-cyano-2-methyl-4-(4-morpholinyl)-4-(4-pyridinyl)butanoate and recrystallizing the product from acetonitrile. The combined samples were recrystallized from isopropyl alcohol using decolorizing charcoal and dried at 120° C. to yield 10 g. of 4,5-dihydro-4-methyl-6-(4-pyridinyl)-3(2H)pyridazinone, m.p. 184°–185° C., tautomeric with 4,5-dihydro-4-methyl-6-(4-pyridinyl)-3-pyridazinol.

Acid-addition salts of 4,5-dihydro-4-methyl-6-(4-pyridinyl)-3(2H)-pyridazinone are conveniently prepared by adding to a mixture of 1 g. of 4,5-dihydro-4-methyl-6-(4-pyridinyl)-3(2H)-pyridazinone in about 20 ml. of aqueous methanol the appropriate acid, e.g., hydrochloric acid, methanesulfonic acid, sulfuric acid, to a pH of about 2 to 3, chilling the mixture after partial evaporation and collecting the precipitated salt, e.g., dihydrochloride, dimethanesulfonate, sulfate, respectively. Also, the monolactate or monohydrochloride acid-addition salt is conveniently prepared in aqueous solution by adding to water with stirring molar equivalent quantitites each of 4,5-dihydro-4-methyl-6-(4-pyridinyl)-3(2H)-pyridazinone and lactic acid or hydrochloric acid, respectively.

Following the procedure described in Example 1 but using in place of methyl 4-cyano-2-methyl-4-(4-morpholinyl)-4-(4-pyridinyl)butanoate a molar equivalent quantity of the appropriate lower-alkyl, preferably, methyl or ethyl, 4-cyano-2-methyl-4-(BN)-4-(4-pyridinyl)butanoate where BN is 1-piperidinyl or 1-pyrrolidinyl, it is contemplated that 4,5-dihydro-4-methyl-6-(4-pyridinyl)-3(2H)-pyridazinone can be obtained.

The preparation of the intermediate lower-alkyl 4-(BN)-4-cyano-2-methyl-4-(4-pyridinyl)butanoate is illustrated as follows for the compound where BN is 4-morpholinyl and lower-alkyl is methyl: To a mixture containing 16 g. of 2-(4-morpholinyl)-2-(4-pyridinyl)ethanenitrile and 150 ml. of tetrahydrofuran in a flask equipped with a stirrer and drying tube was added with stirring 6 ml. of 30% potassium hydroxide in methanol, followed by 8.5 g. of methyl methacrylate. Within thirty minutes an exothermic reaction ensued and a white solid began to separate. The reaction mixture was stirred for one hour and then allowed to stand at room temperature overnight. The reaction mixture was concentrated by heating in vacuo to remove the solvent and the remaining residue was triturated with absolute ether (about 600 ml.) and filtered. The filtrate was concentrated to a volume of about 50 ml., cooled, treated with 50 ml. of n-hexane and chilled. The product that separated was collected and dried at 70° C. to yield 11 g. of methyl 4-cyano-2-methyl-4-(4-morpholinyl)-4-(4-pyridinyl)butanoate, m.p. 93°–94° C.

Following the above procedure described above for preparing methyl 4-cyano-2-methyl-4-(4-morpholinyl)-4-(4-pyridinyl)butanoate but using in place of 2-(4-morpholinyl)-2-(4-pyridinyl)ethanenitrile and methyl methacrylate molar equivalent quantities respectively of the appropriate 2-(BN)-2-(4-pyridinyl)ethanenitrile and lower-alkyl methacrylate, it is contemplated that there can be obtained the following corresponding lower-alkyl 4-cyano-2-methyl-4-(BN)-2-(4-pyridinyl)butanoates: methyl 4-cyano-2-methyl-4-(1-piperidinyl)-4-(4-pyridinyl)butanoate; methyl 4-cyano-2-methyl-4-(4-pyridinyl)-4-(1-pyrrolidinyl)butanoate; ethyl 4-cyano-2-methyl-4-(4-morpholinyl)-4-(4-pyridinyl)butanoate; and, n-propyl 4-cyano-4-(4-pyridinyl)-2-methyl-4-(4-morpholinyl)butanoate.

2. 4,5-Dihydro-6-(4-pyridinyl)-3(2H)-pyridazinone

Following the procedure described in Example 1 but using in place of methyl 4-cyano-2-methyl-4-(4-morpholinyl)-4-(4-pyridinyl)butanoate a molar equivalent quantity of ethyl 4-cyano-4-(4-morpholinyl)-4-(4-piperidinyl)butanoate [McEvoy et al., J. Org. Chem. 44, 4597 (4600)(1979)], it is contemplated that there can be obtained 4,5-dihydro-6-(4-pyridinyl)-3(2H)-pyridazinone.

The following preparation of 4,5-dihydro-6-(4-pyridinyl)-3(2H)-pyridazinone [as its tautomeric 4,5-dihydro-6-(4-pyridinyl)-3-pyridazinol] is described as Example 1 in said copending application Ser. No. 71,064: A mixture containing 2.4 g. of γ-oxo-γ-(4-pyridinyl)butyronitrile, 1.96 g. of hydrazine sulfate, 100 ml. of absolute ethanol and 100 ml. of water was refluxed with stirring overnight (about 15 hours). The reaction mixture was heated in vacuo to remove the solvent mixture. The remaining residue was taken up in water and filtered. The filtrate was neutralized with 10% aqueous sodium bicarbonate solution and a yellow solid separated. The solid was collected, washed with water, dried in vacuo over $P_2O_5$ for four hours. Its nuclear magnetic resonance (nmr) and mass spectra were found to be consistent with that of the desired product but showed traces of impurities. The solid was then recrystallized from absolute ethanol, dried in vacuo over $P_2O_5$ overnight to yield, as golden crystals, 0.9 g. of 4,5-dihydro-6-(4-pyridinyl)-3(2H)-pyridazinone, m.p. 185°–187° C. Its nmr and mass spectra were consistent with the assigned structure.

The above reaction is run by using a molar equivalent quantity of hydrazine dihydrochloride or hydrazine di(methanesulfonate) in place of hydrazine sulfate.

Acid-addition salts of 4,5-dihydro-6-(4-pyridinyl)-3(2H)-pyridazinone are conveniently prepared by adding to a mixture of 1 g. of 4,5-dihydro-6-(4-pyridinyl)-3(2H)-pyridazinone in about 20 ml. of aqueous methanol the appropriate acid, e.g., hydrochloric acid, methanesulfonic acid, sulfuric acid, to a pH of about 2 to 3, chilling the mixture after partial evaporation and collecting the precipitated salt, e.g., dihydrochloride, dimethanesulfonate, sulfate, respectively. Also, the monolactate or monohydrochloride acid-addition salt is conveniently prepared in aqueous solution by adding to water with stirring molar equivalent quantities each of 4,5-dihydro-6-(4-pyridinyl)-3(2H)-pyridazinone and lactic acid or hydrochloric acid, respectively.

The usefulness of 4,5-dihydro-4-R-6-(4-pyridinyl)-3(2H)-pyridazinone or salt thereof as cardiotonic agent is demonstrated by its effectiveness in standard pharmacological test procedures, for example, in causing a significant increase in contractile force of the isolated cat atria and papillary muscle and/or in causing a significant increase in the cardiac contractile force in the anesthetized dog with low or minimal changes in heart rate and blood pressure. Detailed descriptions of these test procedures appear in U.S. Pat. No. 4,072,746, issued Feb. 7, 1980.

When tested by said isolated cat atria and papillary muscle procedure, 4,5-dihydro-4-R-6-(4-pyridinyl)-3(2H)-pyridazinone or pharmaceutically-acceptable acid-addition salt thereof at doses of 10, 30 and/or 100 μg./ml., was found to cause significant increases, that is, greater than 25% in papillary muscle force and significant increases, that is, greater than 25%, in right atrial force, while causing a lower percentage increase (about one-third or less than the percentage increase in right atrial force or papillary muscle force) in right atrial rate. For example, when tested at said dose levels by this procedure, 4,5-dihydro-6-(4-pyridinyl)-3(2H)-pyridazinone (Example 2) was found to cause respective increases of 55%, 89% and 118% in papillary muscle force and respective increases of 30%, 48% and 83% in right atrial rate at 10, 30 and 100 μg./ml. Similarly, 4,5-dihydro-4-methyl-6-(4-pyridinyl)-3(2H)-pyridazinone (Example 1) was found to cause respective increases of 139% and 86% in papillary muscle force and right atrial force at 100 μg./ml. and a papillary muscle force increase of 45% at 30 μg./ml.

The present invention includes within its scope a cardiotonic composition for increasing cardiac contractility, which comprises a pharmaceutically-acceptable carrier and, as the active component thereof, a cardiotonically-effective amount of 4,5-dihydro-4-R-6-(4-pyridinyl)-3(2H)pyridazinone or pharmaceutically-acceptable acid-addition salt thereof. The invention also includes within its scope the method for increasing cardiac contractility in a patient requiring such treatment which comprises administering orally or parenterally in a solid or liquid dosage form to such patient a cardiotonically-effective amount of said 4,5-dihydro-4-R-6-(4-pyridinyl)-3(2H)-pyridazinone or pharmaceutically-acceptable acid-addition salt thereof. In clinical practice said compound or salt thereof will normally be administered orally or parenterally in a wide variety of dosage forms.

Solid compositions for oral administration include compressed tablets, pills, powders and granules. In such solid compositions, the active compound is admixed with at least one inert diluent such as starch, calcium carbonate, sucrose or lactose. These compositions can also contain additional substances other than inert diluents, e.g., lubricating agents, such as magnesium stearate, talc and the like.

Liquid compositions for oral administration include pharmaceutically-acceptable emulsions, solutions, suspensions, syrups and elixirs containing inert diluents commonly used in the art, such as water and liquid paraffin. Besides inert diluents such compositions can also contain adjuvants, such as wetting and suspending agents, and sweetening, flavoring, perfuming and preserving agents. According to the invention, the compounds for oral administration also include capsules of absorbable material, such as gelatin, containing said active component with or without the addition of diluents or excipients.

Preparations according to the invention for parenteral administration include sterile aqueous, aqueous-organic, and organic solutions, suspensions and emulsions. Examples of organic solvents or suspending media are propylene glycol, polyethylene glycol, vegetable oils such as olive oil and injectable organic esters such as ethyl oleate. These compositions can also contain adjuvants such as stabilising, preserving, wetting, emulsifying and dispersing agents.

They may be sterilized, for example, by filtration through a bacteria-retaining filter, by incorporation of sterilizing agents in the compositions, by irradiation or by heating. They can also be manufactured in the form of sterile solid compositions which can be dissolved in sterile water or some other sterile injectable medium immediately before use.

The percentage of active component in the said composition and method for increasing cardiac contractility can be varied so that a suitable dosage is obtained. The dosage administered to a particular patient is variable, depending upon the clinician's judgement using as the criteria: the route of administration, the duration of treatment, the size and condition of the patient, the potency of the active component and the patient's response thereto. An effective dosage amount of active component can thus only be determined by the clinician considering all criteria and utilizing the best judgement on the patient's behalf.

We claim:

1. The method for increasing cardiac contractility in a patient requiring such treatment which comprises administering orally or parenterally in a solid or liquid dosage form to such patient a medicament comprising a pharmaceutically-acceptable carrier and, as the active component thereof, a cardiotonically-effective amount of 4,5-dihydro-R-6-(4-pyridinyl)-3(2H)-pyridazinone or pharmaceutically-acceptable acid-addition salt thereof, where R is hydrogen or methyl.

2. The method according to claim 1 where the active component is 4,5-dihydro-6-(4-pyridinyl)-3(2H)-pyridazinone.

3. The method according to claim 1 where the active component is 4,5-dihydro-4-methyl-6-(4-pyridinyl)-3(2H)-pyridazinone.

* * * * *

UNITED STATES PATENT AND TRADEMARK OFFICE
CERTIFICATE OF CORRECTION

PATENT NO. : 4,486,431

DATED : December 4, 1984

INVENTOR(S) : G.Y. Lesher and W.B. Dickinson

It is certified that error appears in the above-identified patent and that said Letters Patent is hereby corrected as shown below:

Column 8, claim 1, line 48, "R" should read -- 4-R --.

Signed and Sealed this

Third Day of September 1985

[SEAL]

Attest:

DONALD J. QUIGG

Attesting Officer     Acting Commissioner of Patents and Trademarks - Designate